United States Patent [19]
Schafer

[11] Patent Number: 6,012,332
[45] Date of Patent: *Jan. 11, 2000

[54] ULTRASONIC APPARATUS AND METHOD FOR MEASURING ANIMAL BACKFAT

[75] Inventor: Mark E. Schafer, Norristown, Pa.

[73] Assignee: Perceptron, Inc., Plymouth, Mich.

[ * ] Notice: This patent is subject to a terminal disclaimer.

[21] Appl. No.: 09/043,736

[22] PCT Filed: Sep. 25, 1996

[86] PCT No.: PCT/US96/15335

§ 371 Date: Dec. 29, 1998

§ 102(e) Date: Dec. 29, 1998

[87] PCT Pub. No.: WO97/11640

PCT Pub. Date: Apr. 3, 1997

[51] Int. Cl.[7] ............................. G01N 29/06; A61B 10/00
[52] U.S. Cl. ............................. 73/579; 73/615; 73/627; 600/442
[58] Field of Search ............................. 73/579, 584, 597, 73/615, 627, 629; 600/442, 449

[56] References Cited

U.S. PATENT DOCUMENTS

| | | | |
|---|---|---|---|
| 4,138,999 | 2/1979 | Eckhart et al. | 73/597 |
| 4,359,055 | 11/1982 | Carlson | 600/449 |
| 4,646,748 | 3/1987 | Fujii et al. | 128/660 |
| 4,785,817 | 11/1988 | Stouffer | 128/660.07 |
| 5,353,796 | 10/1994 | Schroeder et al. | 128/660.01 |
| 5,613,493 | 3/1997 | Schafer | 600/442 |
| 5,717,142 | 2/1998 | Schafer | 73/597 |

*Primary Examiner*—Max Noori
*Attorney, Agent, or Firm*—Woodcock Washburn Kurtz Mackiewicz & Norris LLP

[57] ABSTRACT

An ultrasonic measuring apparatus (FIG. 2) and method (FIG. 5) to accurately determine the depth of an overlaying backfat (14–20) on an animal (8) without incurring any damage to the animal. The apparatus employs a reverse time analysis approach in which a pulse generator (28) sends a preselected ultrasonic input signal by way of a piezoelectric transducer (16) through the outer skin (12) and successively through each one of the animal's fat layer interfaces (15, 17, 20) to a preselected distance within the loin portion (22) of the animal. This reverse time approach then analyzes the resulting echo signal produced by the input signal sequentially in a direction from this loin portion toward the outer fat layers (14, 16, 18). The first strong signal within a specified range, which depends on the species, breed, age or weight of the animal to be measured, is taken as the bottom-most fat/loin transition. A microprocessor (44) is employed to measure and analyze the amplitude and contour of this signal in a direction toward the loin until it reaches a fixed point that is a prescribed percentage of the peak value of the amplitude of this signal, the magnitude of which depends on the type of animal under measurement. The value derived in this manner is an accurate measurement of the depth of overlaying backfat and is automatically displayed in digital form on a screen (46).

11 Claims, 4 Drawing Sheets

ULTRASONIC APPARATUS AND METHOD FOR MEASURING ANIMAL BACKFAT

BACKGROUND OF THE INVENTION

1. Field of the Invention

The present invention employs a unique ultrasound apparatus to more accurately determine the maximum backfat in any one of a variety of animals even though the number and thickness of their backfat layers are different because of their different species, breeds, ages and weights. As meat packers make their profits from selling lean meat, it is vital for them to purchase live animals, e.g. pigs, that contain a minimal amount of backfat. It is therefore vital that they employ an apparatus that will more accurately measure the backfat of the animals they purchase than any backfat measuring apparatus that is presently available for this purpose.

2. Description of the Prior Art

Prior art backfat measuring devices have used a single ultrasonic beam known as A-mode technology and a swept beam known as B-mode technology. Prior A-mode methods have used simple peak detection and peak counting techniques of the echo signals generated by the fat layers of livestock to determine the total depth of their fat cover. The advantage of A-mode is its lower cost and lower system complexity. Existing systems have also used visual user interpretation of the signal waveforms. B-mode systems have used user interpretation, or some automated means involving lateral pattern recognition. However, B-mode systems with this feature currently require an external computer interface and analysis equipment. Therefore, these B-mode systems are too costly and too complex to satisfy present-day purchasers of such equipment.

Present day A-mode systems fail to completely solve this problem because when an input signal is transmitted into the backfat of an animal the resulting amplitude of the reflected peak of the signal that is detected by present day techniques are often in error due to the variability of the tissue reflection strength, causing either false returns if the detection level is too low, or missed returns if the peak detection threshold is too high. Further, in most livestock species, especially pork, the number of fat layers increases with increasing fat thickness. Therefore a peak-counting procedure can be in error. In addition, the final tissue interface between fat and muscle, which is the most important one in terms of fat thickness measurement, is generally not a distinct, thin layer, but an extended region of connective tissue. The peak of the ultrasound signal returned from this type of layer does not adequately quantify the extent of the layer, which leads to errors unacceptable in the present-day market.

Prior art systems, for example Carlson (U.S. Pat. Nos. 4,359,055 and 4,359,056), use peak detection circuitry to find the location of the peak of each echo signal returned as a result of ultrasonic pulses that have been transmitted into the animal through a transducer. However, there is an error in this approach because this approach identifies the peak of the echo signal as the depth to the fat/loin interface, whereas the true fat/loin interface is at a substantial percentage below the peak. The fact that the fat/loin interface is below the peak was shown to be true in an accreditation test by the National Swine Improvement Federation in January 1995. The federation certified operators using the system disclosed herein which uses this below-the-peak measurement approach to have a high degree of accuracy in backfat measurements when compared to actual carcass data.

SUMMARY OF THE INVENTION

The object of this invention is to employ an apparatus and method that uses ultrasound signals reflected from layers of backfat within livestock animals, e.g. swine, cattle, and sheep, to accurately determine the depth of the fat layer by properly accounting for the nature of the fat/loin interface within the animal which varies with the animal's species, breed and weight. The apparatus as disclosed herein is not subject to errors in the measurement of the depth of the fat layers as the number of fat layers change in an animal with increasing age. The prior art approaches consider the reflection time signal strength history of using a reflected signal as a function of receive time using forward time analysis. In other words, decisions are made with regard to the interface positions starting from the transducer and proceeding further into the animal when using these prior art devices. On the other hand, the present invention uses a reverse time approach in which the signal is analyzed from deeper to shallower depths of fat, and the first strong signal within a specified range, such range to be dependent upon the animal to be measured, is taken as the bottommost fat/loin layer transition. This is the fat to loin transition. This removes the ambiguity which arises when there are different layers of fat as a function of animal's age, weight and fat characteristics.

Once the signal which corresponds to the deepest fat layer is so identified, the location of the deeper edge of the signal, not the location of its peak, is taken as the fat/loin interface. This is because the tissues which make up the fat/loin interface are not well defined and produce indistinct echo patterns rather than sharply defined peaks. Therefore, the reflection must be considered an extended time signal, and the true interface between fat and loin is found at the trailing, or deeper edge of the signal. The deeper edge location derived from experimental research is defined as that point which is proportionally lower than the peak. For example, the point on the trailing edge of the signal which is 30% of the peak value was determined by experimentation to represent the true fat/lean interface of swine. This 30% level on which this trailing edge is located is shown in FIG. 4 of the drawing as the Threshold Level.

DETAILED DESCRIPTION OF THE INVENTION

Figure 1:
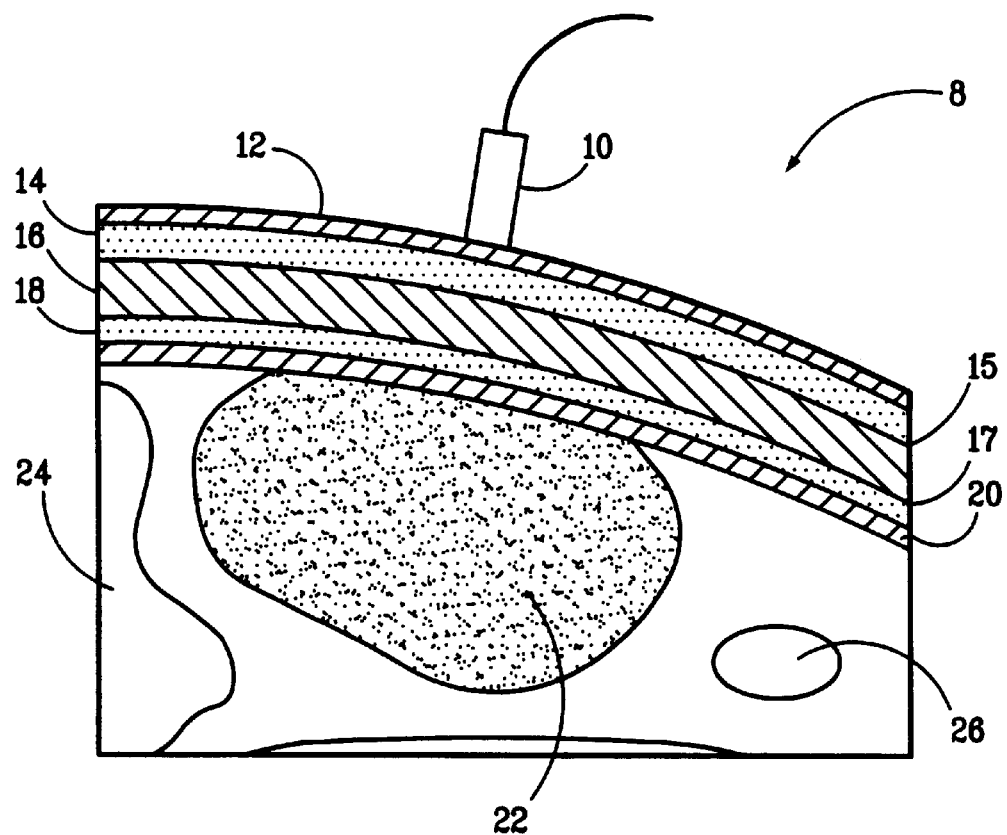
FIG. 1 is a sectional view through a portion of the animal's back with the transducer probe in place.

FIG. 1 shows a typical cross sectional view of the backfat and loin of an animal such as a hog 8. The ultrasound transducer 10 is applied to the outer intact skin surface 12 of the animal, with a coupling fluid such as oil. The transducer emits and receives ultrasound pulses which reflect from the various tissue layers within the animal. The first fat layer 14 is typically six to ten millimeters in depth and is separated from the second fat layer 16 by a thin membrane 15. Similarly, the second and third backfat layers 16 and 18 are separated by a thin membrane 17. The third or additional backfat layers only appear in certain species and breeds and at certain ages and weights. Thus, the number and thicknesses of the different fat layers can change significantly from one animal to another, from one breed to another, and by species. The border between the last fat layer 18 and the beginning of the loin muscle 22 is denoted as 20. FIG. 1 shows backbone 24 and rib bone 26 which can be used to provide orientation of the loin muscle. The invention accurately quantifies the depth to the beginning of the loin muscle 22 or, in other words, the bottom of the interface 20 by analyzing the ultrasound signals reflected back to transducer 10.

Figure 2:
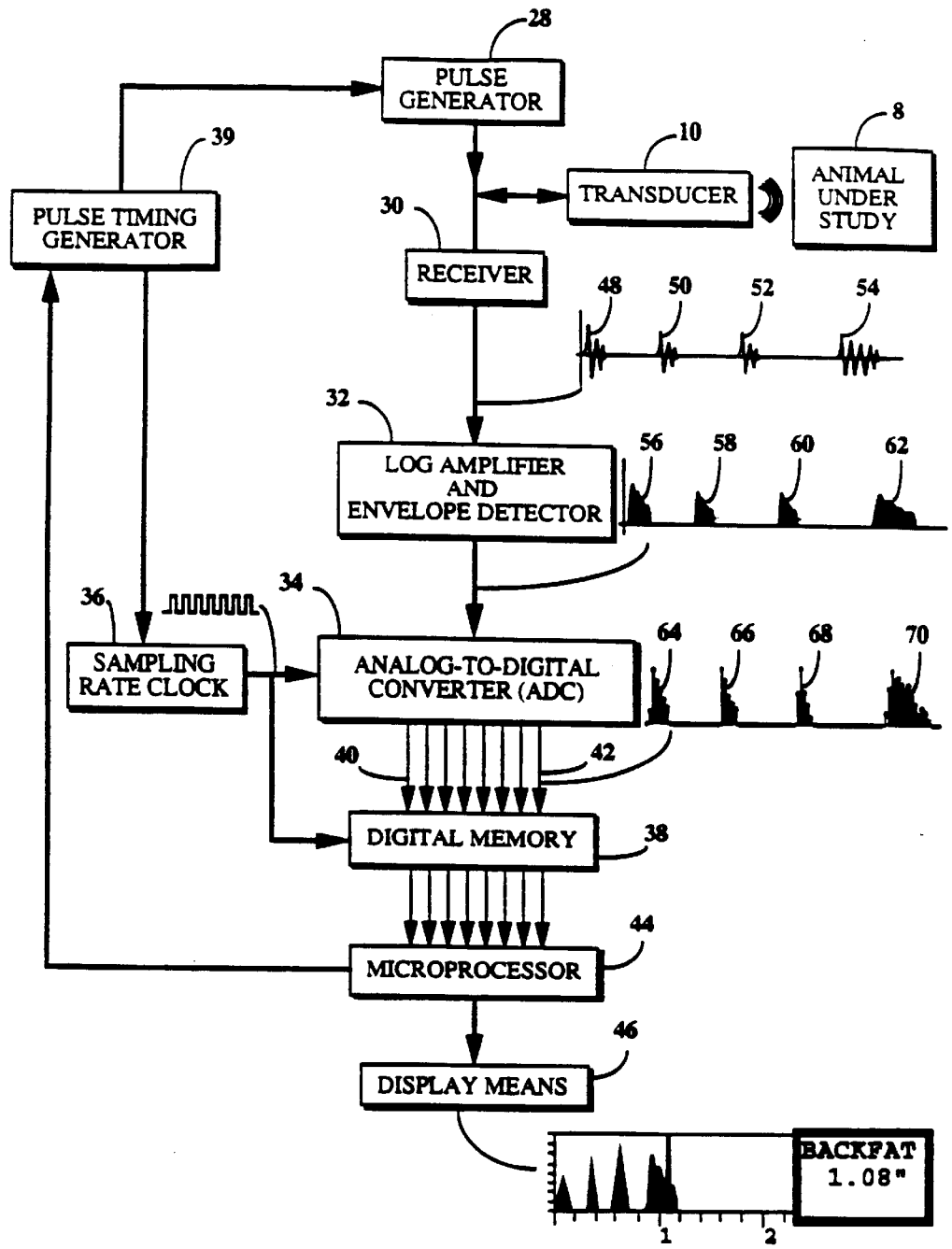
FIG. 2 is a flow diagram which shows the components of the present invention.
Figure 3:
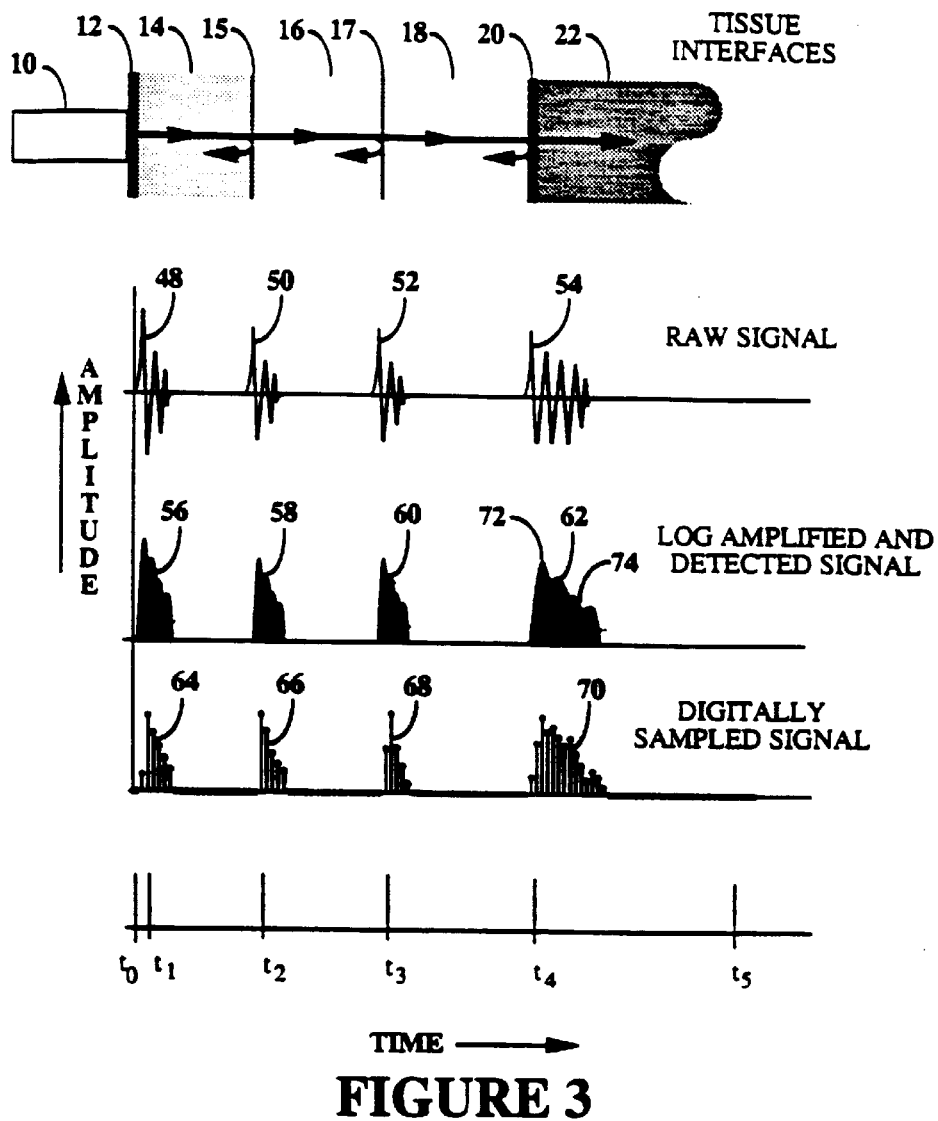
FIG. 3 shows an arrow indicating an ultrasonic input signal transmitted through backfat and the fat/loin interface and how the responding output signals are modified by the system components over various time response periods.

FIG. 2 shows an apparatus to accurately quantify the depth to the beginning of the aforementioned loin muscle 22 or, in other words, the bottom of the interface 20 by analyzing the ultrasonic signal reflected back to transducer 10. FIG. 2 shows the components for executing the principles of the invention. A pulse generator 28 is used to excite the ultrasound transducer 10. The transducer 10 emits an A-mode ultrasound wave into the tissue and this ultrasound energy in the form of an echo signal is reflected back to the transducer 10 at each tissue interface 15, 17, 20 as shown in FIGS. 1 and 3. The signals received at the transducer 10 is amplified by receiving circuits 30. The received signals are logarithmically amplified and enveloped by detector 32 before being converted into a fully digital form by the analog to digital converter, ADC, 34. The sampling rate of the ADC 34 is set by a clock circuit 36 which establishes the temporal resolution of the system. Since in this type of system travel time of the ultrasonic wave is related to travel distance, the clock 36 also sets the spatial resolution of the system. The time duration of the transmitted pulse is thus also a factor of the spatial resolution. The clock circuit 36 also sequences the digital memory circuit 38. The clock is started at the same time as the transmitting pulse so there is proper time synchronization. The exact number of clock cycles and thus the size of the digital memory circuit 38 depends upon the sampling rate and the desired depth of tissue to be measured.

FIG. 2 shows a number of electrical connections; e.g., 40, 42, between the ADC 34 and the digital memory 38 to represent the number of bits and resolution of the ADC 34. At least six bits of resolution are required and eight bits are generally desired in utilizing this system. Because the clock 36 is synchronized with the pulse 4 generator 28 and the clocking frequency is known, each sample within the digital memory 38 corresponds to a specific time from the time of the ultrasonic waveform. Thus, each sample within the digital memory corresponds to a specific depth within the fat layers forming the backfat of the animal. The depth and the time are related by the speed of sound in the backfat which is generally taken at 1540 meters per second.

Once a single received waveform is stored in the digital memory 38 it is read and analyzed using the microprocessor 44 which can, for example, be a 8051 family of microcontrollers, for instance, the DS80C320 from Dallas Semiconductor. The microprocessor 44 drives a display means 46 which communicates the results of the measurements to the user. The display is a full graphic display of the waveform and may be implemented using a graphic LCD display such as the HG 24501 from Hyundai Electronics.

In order to explain further how the apparatus functions, reference is now made to FIG. 3. The trace shown in the upper portion of FIG. 3 represents the received ultrasound signals 48, 50, 52 and 54 as a function of time as produced by the receiver circuit 30 as a result of the signal it receives from the transducer 10. The trace shown in the lower portion of FIG. 3 shows the log amplified and detected signals 56, 58, 60 and 62 corresponding to the reflection of the interface between the animal's skin 12 and fat layer 14 and interfaces 15, 17 and 20, respectively, as shown in FIG. 1. After logarithmic amplification and detection, the signals which correspond to 48, 50, 52 and 54 are 56, 58, 60 and 62, respectively, which in turn are then converted into the digitally sampled signals 64, 66, 68 and 70 shown in FIG. 3. It can be seen that the signals 54 and 62 are of extended time duration relative to the other signals.

Figure 4:
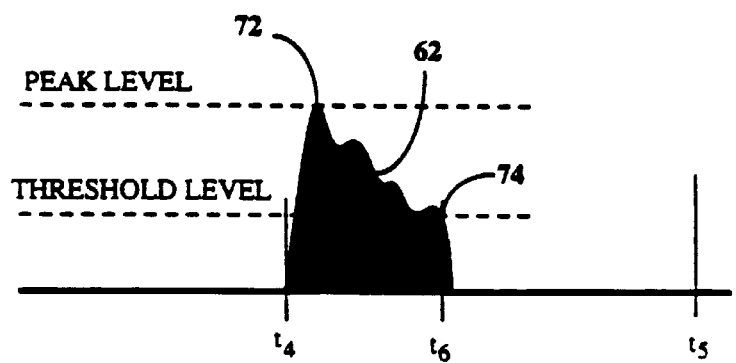
FIG. 4 shows in graphic form how the apparatus of FIG. 2 can precisely determine the backfat of an animal.

FIG. 4 shows how to repeatedly and reliably determine the extent of signal 62 and thus, the exact point of the beginning of the loin muscle 22 or, in other words, the depth of maximum backfat at interface 20 as shown in FIG. 1. The apparatus as shown in FIG. 2 thus correctly identifies the signal which corresponds to interface 20 irrespective the number of intervening fat layers.

FIG. 4 further shows an expanded view of the signal 62 and time interval $t_4$ to $t_5$. The apparatus shown in FIG. 2 starts by examining the signal in reverse time order; that is, from $t_5$ to $t_4$ as shown in FIG. 3. Time $t_5$ is selected by previous experimentation for the specific species of animal to be measured and is such that it will always be located at a point beyond the deepest fat thickness of that species. Experimental research has determined that for market hogs in the weight of two hundred to two hundred eighty pounds, the deepest backfat thickness is 2.4 inches and therefore, this $t_5$ as shown in FIG. 3 is set to a time corresponding to 2.5 inches. Starting at time $t_5$ in FIG. 3 and working toward time to, the echo signal 62 becomes the first echo, thus removing the ambiguity caused by the variability in the number of echoes such as 58 and 60. The apparatus shown in FIG. 2 next performs a search for a peak of the echo signal 62 and finds the point labeled 72 as identified in FIG. 4. Once this point 72 is located and this peak level is found, the apparatus of FIG. 2 next searches back in the direction of $t_5$ until the signal level falls below a threshold level as indicated by reference numeral 74. This threshold level is taken as a percentage of the peak level. In this way, variations in the absolute signal level are not important since the threshold is always set as a percentage of the peak level. The particular percentage of the peak level employed for hogs has been found through experimentation to be 30%. This percentage was found to best represent the true fat/muscle interface when compared to actual carcass data measurements.

Figure 5:
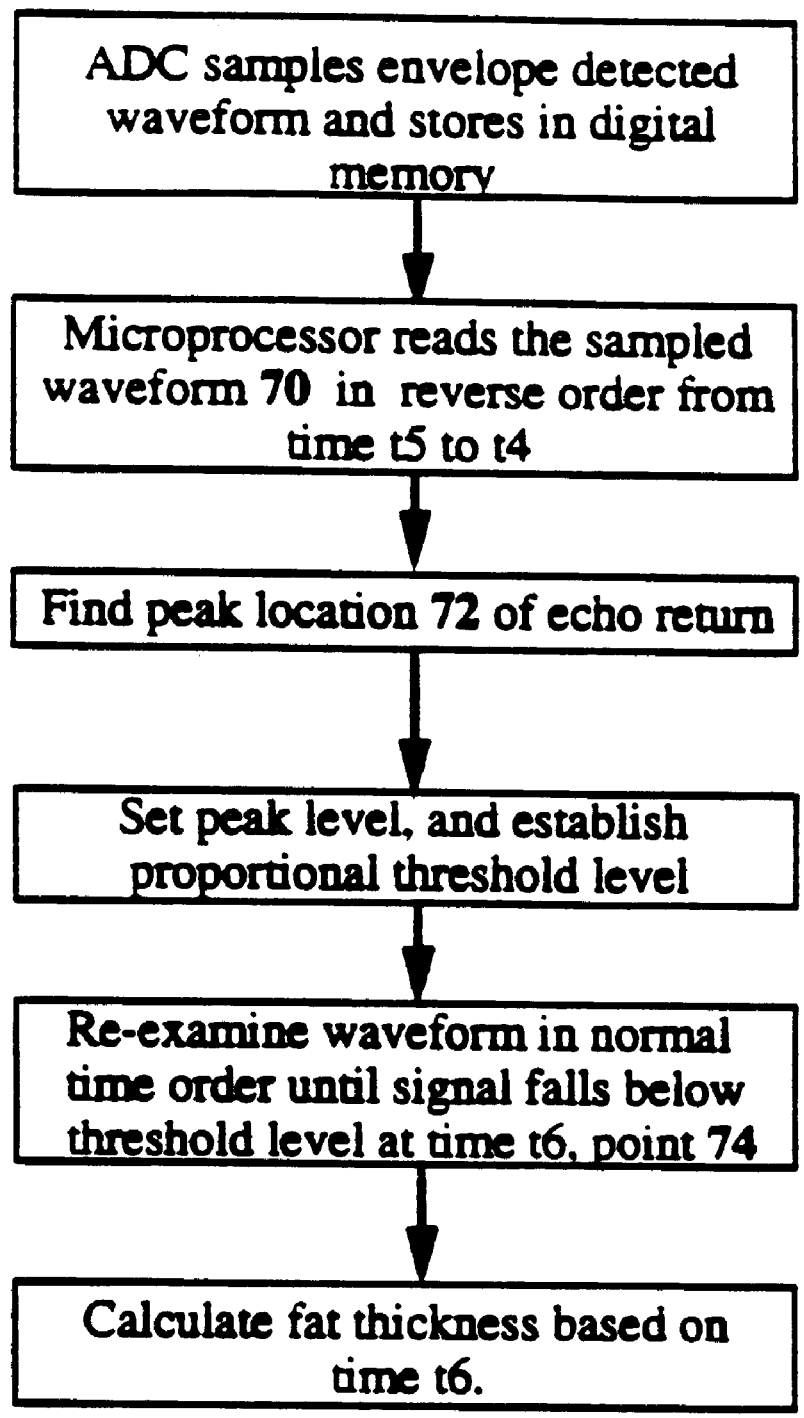
FIG. 5 shows the sequential steps the apparatus of FIG. 2 takes in very accurately determining the backfat of an animal.

FIG. 5, which is self-explanatory, shows the most important steps in the order of execution which components of the apparatus shown in FIG. 2 employs to obtain the maximum amount of backfat in an animal.

Summarizing, it can be seen that the use of the aforementioned unique reverse time approach for measuring the depth of backfat of an animal is preferred over any other animal backfat measuring device that is presently available because:

(a) It has been tested, shown and accepted in meat producer tests to produce the most accurate measurement of backfat of any of the backfat measuring devices that are presently available;

(b) Meat packers with this measuring device will be able to more accurately select for purchase animals which possess a minimal amount of backfat and they will therefore experience a greater return on their investment due to less fat waste when they dress these animals for consumer use;

(c) Because this reverse time backfat depth measuring system is constructed to take into account changes in the nature of the fat/loin interface in an animal due to its species, breed and weight, a more accurate measure of the depth of the backfat of an animal is achieved than prior art backfat measuring devices because they are not designed to compensate for these changes;

(d) This reverse time backfat depth measuring system is unique because it first identifies the peak level of the echo response signal representative of the deepest fat layer adjacent the fat/loin interface of the animal. It then moves downward along the trace of this signal to identify a point on a threshold level that is located at a fixed preset percent of the peak, e.g., 30% for swine, and will therefore accurately measure the depth of animal backfat though the tissues that make up the fat/loin interface which is not as well defined as other fat interfaces. This reverse system is used to measure the depth of backfat by using this threshold level measuring technique and has in practice been shown to be a much more accurate measurement of the depth of backfat in an animal than prior devices that use the amplitude of peak echo response signals per se; and (e) The system disclosed herein provides numerous depth of fat measurements in a more accurate and more stable manner over a long period of time than prior art devices.

What is claimed is:

1. A system using a reverse time approach to accurately measure and indicate the thickness of backfat in an animal, comprising:

a pulse generator which generates an excitation signal;

a transducer responsive to said excitation signal to convert said excitation signal into an ultrasonic wave signal, to transmit said ultrasonic wave signal through the outer skin and backfat of said animal and then off of a backfat/loin interface of said animal, and to receive a responding ultrasonic echo signal;

a receiver which amplifies the responding ultrasonic echo signal reflected from the backfat/loin interface and converts said ultrasonic echo signal into an electrical echo signal;

a microprocessor operable to measure a peak of said electrical echo signal that is representative of the maximum amplitude of the responding ultrasound echo signal reflected from said fat/loin interface, said microprocessor being further operable to select a prescribed point on said electrical echo signal that is below said peak that represents an accurate measurement of the thickness of backfat in said animal; and a display operably connected to said microprocessor which visually indicates the thickness of backfat in said animal.

2. A system as in claim 1, further comprising a pulse timing generator responsive to said microprocessor, said pulse timing generator generating timing signals for synchronizing the transmitting and receiving functions of said system.

3. A system as in claim 2, further comprising a log amplifier and envelope detector which amplifies said electrical echo signal in a logarithmic manner, a sampling rate clock responsive to a timing signal from said pulse timing generator, an analog to digital converter which converts said amplified electrical echo signal into a digital echo signal at a sample rate determined by said sampling rate clock, and a memory which stores said digital echo signal for processing by said microprocessor.

4. A system as in claim 1, wherein the animal is a member of the swine family and the prescribed point on said electrical echo signal that is below said peak is a point on said electrical echo signal having an amplitude that is approximately 30% less than the amplitude of said peak signal.

5. A system as in claim 1, wherein said ultrasonic wave signal is a single A-mode beam.

6. A system as in claim 1, wherein said transducer is a piezoelectric transducer and oil is used as a coupling fluid to transmit said ultrasonic wave signal through the outer skin of said animal and to receive the responding ultrasonic echo signal from the outer skin of said animal.

7. A system as in claim 6, wherein the piezoelectric transducer is placed on a loin of the animal in close proximity to the backfat/loin interface.

8. A system as in claim 1, wherein, when the animal is a hog weighing between 200 and 280 pounds, a threshold for a maximum backfat thickness of said animal between the skin and fat/loin interface is set to 2.5 inches, whereby a last peak in said electrical echo signal before said threshold is processed by said microprocessor to determine the thickness of the backfat of the animal.

9. A reverse time system for accurately measuring the depth of backfat in an animal, comprising:

means for sending an ultrasonic input signal of a predetermined time duration through the skin of said animal so as to extend through its backfat into a loin portion thereof and for receiving an echo signal from a backfat/loin interface of the animal regardless of the species, breed, age, weight or number of fat layers the animal possesses;

means for sensing the amplitude of the peak of the echo signal generated by the backfat/loin interface, for determining a point on said echo signal having an amplitude which is a predetermined percentage of the amplitude of the peak, said point being related to at least one of the species, breed, age, weight, or number of fat layers of the animal, and for converting a waveform representing a time value of said point on said echo signal into a measurement of the depth of backfat possessed by the animal; and means for displaying said backfat depth.

10. A system as in claim 9, wherein the animal is a member of the swine family and said point on said echo signal has an amplitude that is approximately 30% less than the amplitude of said peak signal and is adjustable for different animals in accordance with experimental research regarding the species, breed, age, weight or number of fat layers of the different animals.

11. A method of accurately measuring the depth of the backfat in an animal, comprising the steps of:

transmitting an ultrasonic input signal through the backfat and loin interface of the animal;

sampling a responding echo waveform from the backfat/loin interface of the animal and storing the sampled echo waveform in a memory;

reading the sampled echo waveform in reverse time order from the memory for echo samples from the loin toward echo samples from the fat/loin interface;

locating a peak amplitude in the sampled echo waveform generated by the fat/loin interface;

selecting a prescribed percentage of the amplitude of the peak that is characteristic of the type of animal under measurement;

reading the sampled echo waveform in a forward time order from said peak until a point is found having an amplitude that is approximately said prescribed percentage of the amplitude of the peak; and determining the depth of the backfat in the animal based on the response time corresponding to the point in said echo waveform having an amplitude that is approximately said prescribed percentage of the amplitude of the peak.

* * * * *